United States Patent [19]

Moebus et al.

[11] 4,447,534

[45] May 8, 1984

[54] METHOD OF PRODUCING ETHANOL THROUGH FERMENTATION OF CARBOHYDRATES

[76] Inventors: Otto Moebus, Lämmerstücken 36, Kiel-Russee; Michael Teuber, Gartenstr. 114, Flintbek; Helmut Reuter, Dorfstede 23, Kiel-Schulensee, all of Fed. Rep. of Germany

[21] Appl. No.: 344,937

[22] Filed: Feb. 2, 1982

[30] Foreign Application Priority Data

Feb. 16, 1981 [DE] Fed. Rep. of Germany ....... 3105581

[51] Int. Cl.$^3$ .............................................. C12P 7/06
[52] U.S. Cl. .................................. 435/161; 435/288; 435/813; 435/940
[58] Field of Search .............. 435/160, 161, 178, 182, 435/288, 813

[56] References Cited

U.S. PATENT DOCUMENTS 4,048,018 9/1977 Coughlin et al. ................ 435/813 X
4,350,765 9/1982 Chibata et al. ....................... 435/161

OTHER PUBLICATIONS

Advances in Biotechnology Young, Pergamon Press, 1981, pp. 635–641.

*Primary Examiner*—Ferris H. Lander
*Attorney, Agent, or Firm*—Wenderoth, Lind & Ponack

[57] ABSTRACT

Residue-free production of ethanol and unicellular protein in a gas-fluidized bed, in which ethanol production takes place in a gas-fluidized bed (stirred fluidized bed, fluid column), the particle fraction of which consists of a wet microorganism mass, e.g. *Saccharomyces cerevisiae*. A nutrient solution with fermentable carbohydrates is sprayed onto the fluidized particles. The ethanol, which evaporates with the water, is precipitated in a condenser on the discharge side, so that the fluidized bed serves as bio-reactor as well as one-stage distillation plant (together with the cooling system). Thus, the mash column, which is normally used for alcohol production with the submersion method, is not needed in the present invention. In place of the residue, a protein-rich product with 30–40% dry mass is formed, which, during continuous operation, can be removed at certain intervals from the bioreactor and can be dried to the desired degree. The propagation of the microorganisms can be regulated through the oxygen content of the gas phase; the ethanol production can be regulated through the infeed of the nutrient solution. The gas used for fluidization is recirculated into the bed. The partial oxygen pressure can be controlled by adding other gases to the air, such as nitrogen or carbon dioxide, particularly carbon dioxide, which forms the yeast itself.

12 Claims, 1 Drawing Figure

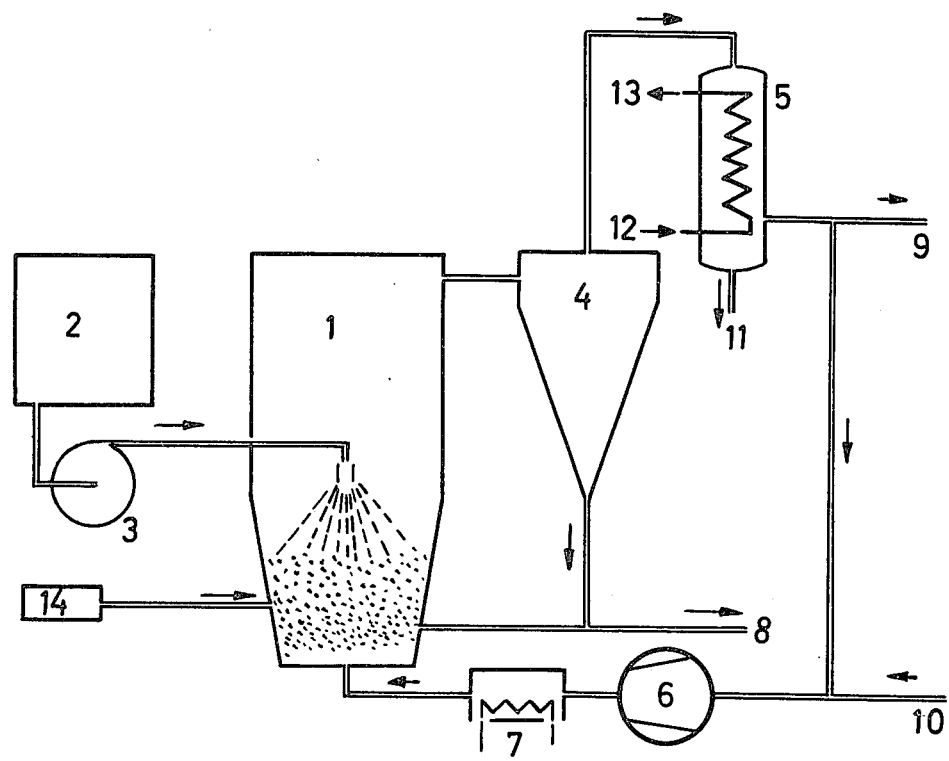

METHOD OF PRODUCING ETHANOL THROUGH FERMENTATION OF CARBOHYDRATES

BACKGROUND OF THE INVENTION

The biotechnological process of producing ethanol in alcohol distilleries is done such that a mash of hydrolyzed, carbohydrate-containing material is fermented and subsequently completely freed of alcohol in a mash column by heating it directly with steam, and the escaping water-alcohol mixture is fed into a rectifying column. A residual solution is discharged from the mash column, which presents an environmental problem. According to a DECHEMA study on research and development in the field of biotechnology, pp. 121-122, which was done in 1974 by order of the Federal Ministry for Research and Technology in Germany, approximately 2 million m$^3$ of residue from starchy raw materials accumulate each year in the Federal Republic. This residue contains 25 000 mg $O_2$/l, which represents a very high BSB$_5$ value (biochemical oxygen requirement for a 5-day period). The residual materials cannot be stored and can only be used directly as feed. It would be desirable to have the product dried in order to use it as feed admixture. According to K. R. Dietrich (see H. Kretzschmar, "Yeast and Alcohol," Springer publication, Berlin, Göttingen Heidelberg, pp. 506 to 509, 1955), the residue, which is discharged at the bottom of the mash column, can be led over a strainer, the resulting solid materials can be pressed, the accumulating fluid can be boiled down in a multi-evaporator and the concentrated mass can subsequently be dried with the aid of drum dryers. According to the above mentioned DECHEMA study, such a drying process is not economical in the Federal Republic for energy-political reasons and in view of the size of such operations.

SUMMARY OF THE INVENTION

It is one of the tasks of this invention to produce ethanol under processing conditions, which prevent the accumulation of a watery residue.

According to the invention, ethanol production takes place in a gas-fluidized bed (stirred fluidized bed, fluid column), the particle fraction of which consists of a wet microorganism mass, such as *Saccharomyces cerevisiae*. It is preferable to spray a nutrient solution with fermentable carbohydrates, for example hydrolyzed starch and/or hydrolyzed cellulose, onto these fluidized particles.

The ethanol, which evaporates with the water, is precipitated in a condenser, coupled on the outlet side, so that the fluidized bed serves as bioreactor as well as one-step distillation plant, together with the cooling system. The mash column, used for alcohol production with the submersion method, is therefore not needed for the invention-based method. In place of the residue, a protein-rich product with 30-40% dry mass is produced. During continuous operation, this product can be removed from the bioreactor at certain intervals and further dried to the desired degree.

The propagation of the microorganisms is controlled through the oxygen content of the gas phase, the ethanol formation through the supply of nutrient solution. The gas, which is used for fluidization, is preferably recirculated into the bed. The partial oxygen pressure can be controlled by adding other gases to the air, such as nitrogen or carbon dioxide, especially carbon dioxide, which forms the yeast itself.

In particular, carrying out the ethanol production according to the invention in a gas-fluidized bed, with subsequent condensation of the water-alcohol mixture, has the advantage of making the mash column, needed so far, unnecessary. Together with the cooling system, the gas-fluidized bed will take over the function of the first distillation stage. No watery residue accumulates, and surplus yeast as well as the remaining unfermented substrate can be removed in granular form from the fluidized bed. The granular material contains only as much water as is needed to maintain the enzyme functions of the microorganisms (e.g. yeast). In a subsequent drying process—for batch processes in the same plant, for continuous operation in a second stage—the granular material can be dried to the desired degree.

It may be of advantage economically that the proposed method is set up as a combination method for the production of ethanol as well as the production of unicellular protein. When using yeast (*Saccharomyces cerevisiae*), the amount of unicellular protein, which accumulates with the granular material, can be increased at the expense of the ethanol yield by increasing the partial oxygen pressure in the gas used for fluidization (Pasteur effect). A decrease in the yield of unicellular protein in favor of an increase in the ethanol production can be achieved, even with increased partial oxygen pressure in the fluidized bed, by adding a surplus amount of glucose (crabtree effect).

With the conventional batch process for alcohol production, the fermentation rate decreases more and more with the increase in alcohol concentration in the mash because a higher alcohol concentration will inhibit the enzyme action of the yeast. In the system displayed here, the alcohol is continuously evaporated from the particle surface, along with the gas flow, which keeps the alcohol concentration in the particles low and makes it possible for the fermentation to take place at maximum speed. According to Kretzschmar ("Technical Microbiology," Paul Parey, Berlin, Hamburg, p. 36, 1968), under the conditions of a technical fermentation, the alcohol concentration in the evaporated water (that is the ethanol concentration in the condensate) is approximately ten times higher than that in the concentration from the fermenter.

Cooling of the fermentation tank, which is necessary with the conventional alcohol production, is not needed for the fluidized-bed production because the heat, which develops, is used immediately to evaporate the water (see O. Moebus, M. Teuber and H. Reuter, German Patent 28 45 387).

It may also be possible to produce ethanol with the fluidized bed method for the purpose of using it as a fuel, and on the basis of sugar beets, as proposed by K. D. Kirby and C. J. Mardon (Biotechnology and Bioengineering 12, pp. 2425-2427, 1980).

BRIEF DESCRIPTION OF THE DRAWING

In the following, the invention is described with the aid of an operational example with reference to the accompanying drawing, the single FIGURE of which is a diagram of a plant for carrying out the invention.

The drawing shows a plant for combined ethanol-unicellular protein production in a fluidized bed (1), which at the beginning is charged with floating microorganism particles from (14) and which is then fed substrate from a supply container with carbohydrate-containing, watery nutrient solution (2), with the aid of a pump (3) with a spray-nozzle, which is installed above the fluidized bed. With the aid of precipitator (4), solid materials, discharged from the bed, are precipitated. The upper part of the precipitator contains an $O_2$ electrode, used to measure the partial $O_2$ pressure in the gas (not shown). The unicellular protein particles, discharged from the fluidized bed, and the solid contents from the precipitator can be gathered in one fraction (8). The water-alcohol mixture is condensed in a cooler (5) and removed at (11). The gas can be cooled either with well water or with ice water. The water enters at (12) and is discharged at (13). Outside gas (10) or the recirculated gas from the fluidized bed is sucked in by a ventilator (6), heated over a heating system (7) and blown into the bed. At point (9), cooled gas can escape.

The amount of water to be evaporated per unit of time from the fluidized bed and/or the water content of the fluidized bed can be controlled by controlling the water-vapor-gas mixture dew point in the cooling system for the gas to be recirculated, or the amount of water evaporated per unit of time from the fluidized bed can be regulated by a heating element and the amount of heat discharged to the gas removed from the fluidized bed. The ethanol/water mixture precipitated by the cooling step can be fed into a rectifying column to remove ethanol from the mixture.

For the two technical experiments described in the following, the nutrient solution, fed in through pump (3), contained 250 g glucose ("Maizena," a commercial product with added vitamins), 10 g yeast extract, 4.5 g $KH_2PO_4$, 1.0 g $MgHPO_4.3H_2O$ and 0.2 g $CaCl_2.2H_2O$. The following conditions existed in the fluidized bed for this experiment: gas velocity inside the bed was 0.54 m/s; the gas temperature before entering the bed was 45° C.; relative humidity of the gas prior to entering the bed was 10%; the gas temperature following escape from the bed was 19° C. The cooling water temperature was 1° C. before entering the cooler and 6° C. after leaving it; the amount of cooling water used was 450 l/h. By feeding nitrogen into the plant, the $O_2$ content of the gas was adjusted to 7% during the first experiment. During the second, the $O_2$ content of the recirculated gas was 0%. The amount of yeast used was 2.930 kg in the first experiment and 2.817 kg for the second experiment. The yeast, made by the UNIFERM company in Monheim, Germany is crumbled in a food processor in order to improve the fluidity of the particles, 0.8% Cab-o-sil by the Cabot Company (pyrogenic silicic acid). The result of the analysis were:

(1.) Results of the first experiment (7% $O_2$ in the gas): for each nutrient solution, for which 226.6 g glucose/l were determined through enzyme analysis, 29.8 g ethanol and 48.3 g dry yeast substance (DYS) formed. Ethanol production was 10.7 g ethanol/kg particles and per hour and, for a specific particle weight of 0.9, we obtained 11.9 g ethanol/l particle per hour were obtained. The theoretical glucose requirement for ethanol production (with a factor of 1.956) was 58.3 g glucose/l nutrient solution, for the dry yeast substance formation (with a yield coefficient of 0.456 g DYS/100 g glucose, obtained under fully aerobic conditions) it was 105.9 g glucose/l nutrient solution, and for the remaining glucose in the particles, 0.4 g glucose/l per l nutrient solution after conversion was obtained. Accordingly, we obtained a technical yield of 73% when applied to the amount of glucose used was obtained. The experiment lasted 4.73 hours.

(2.) Results of the second experiment (0% $O_2$ in the gas): per 1 nutrient solution with 237.0 g glucose/l (enzyme analysis), 52.9 g ethanol and 35.3 g DYS were formed. Ethanol production was 20.7 g ethanol/kg particles per hour and/or 23.0 g ethanol/l particles per hour. The theoretical glucose requirement for ethanol production was 103.5 g/l nutrient solution and 77.4 g/l nutrient solution for DYS formation. The remaining glucose value in the particles was 9.0 g, converted for 1 l nutrient solution. Applied to the amount of glucose used, a technical yield of 80% was obtained. The experiment lasted 5.65 hours.

Mssrs. Moo-Young, J. Lamptey and C. W. Robinson (Biotechnolgy Letter, 12, pp. 541 548, 1980) determine that an ethanol productivity of 21.8 g/l.h with use of carrier-combined Saccharomyces cerevisiae, the value of which is within the range of the second experiment, above, in a submersion systems, can be obtained under optimum conditions if the cellular mass is returned to the fermenter (18–32 g/l.h).

Based on the enzyme method, the ethanol analysis in the condensate (2nd experiment) had the following results (ethanol-UV-test, Boehringer, Mannheim): 48.4 g ethanol/l condensate, based on the colorimetric method through oxidation with bichromate in a sulfuric acid solution (B. Lange, "Calorimetric Analysis," publisher: Chemie, Weinheim-Bergstr. p. 274 and 275, 1952), and 48.0 g ethanol/l condensate. Because the first method specifically determines ethanol, the second method generally measures the evaporated substances, which can be oxidized, and it can be assumed that under the selected fermentation conditions, ethanol is the main product besides the biomass, and that other fermentation products do not enter the system quantitatively.

We claim:

1. A method of producing ethanol by fermentation of carbohydrates, which comprises:
   maintaining a gas-fluidized bed of microorganisms suitable for ethanol production,
   adding at least one fermentable, carbohydrate-containing watery nutrient solution to said fluidized bed,
   conducting fermentation in said fluidized bed while introducing gas into said fluidized bed as a continuous phase, the conditions of said fermentation being essentially provided by the termperature and partial oxygen pressure of said gas,
   removing a portion of said gas from said fluidized bed,
   cooling and fractionating said removed gas to precipitate an ethanol/water mixture from said gas, and removing ethanol from said mixture.

2. A method in accordance with claim 1, wherein the gas, which flows into the fluidized bed, is heated with a heating element before entering the bed.

3. A method in accordance with claim 1, wherein unfermented biomass, together with remaining unfermented nutrients, are removed from the fluidized bed in the form of wet granules, and the granules are subsequently dried.

4. A method in accordance with claim 1, wherein Saccharomyces species are used as the microorganisms.

5. A method in accordance with claim 1, wherein unicellular protein is also produced during the fermentation.

6. A method in accordance with claim 5, wherein the ratio of produced ethanol to synthesis of unicellular protein is adjusted by controlling the partial oxygen pressure in the continuous gas phase.

7. A method according to claim 6, wherein nitrogen and/or carbon dioxide are fed into the fluidized bed to adjust the partial oxygen pressure.

8. A method according to claim 6, wherein air is added to the fluidized bed, oxygen in the air is partially or totally used up by the microorganisms during the fermentation, and the resultant refined air is recirculated into the fluidized bed.

9. A method in accordance with claim 1, wherein the nutrient solution contains hydrolyzed starch and/or hydrolyzed cellulose.

10. A method in accordance with claim 1, wherein after precipitating the ethanol/water mixture from the gas, the resultant gas is recirculated to the fluidized bed, and the amount of water to be evaporated per unit of time from the fluidized bed and/or the water content of the fluidized bed is controlled by controlling the water-vapor-gas mixture dew point in the cooling step for the gas to be recirculated.

11. A method in accordance with claim 1, wherein the ethanol/water mixture precipitated by the cooling step is fed into a rectifying column to remove ethanol from the mixture.

12. A method in accordance with claim 1, wherein the amount of water evaporated per unit of time from the fluidized bed is regulated by a heating element and the amount of heat discharged to the gas removed from the fluidized bed.

* * * * *